US012274863B2

(12) United States Patent
Holmqvist et al.

(10) Patent No.: US 12,274,863 B2
(45) Date of Patent: Apr. 15, 2025

(54) MEDICAMENT CONTAINER HOLDER (71) Applicant: SHL MEDICAL AG, Zug (CH)

(72) Inventors: Anders Holmqvist, Värmdö (SE); Linda Odelberg, Ekerö (SE); Anders Boström, Solna (SE)

(73) Assignee: SHL Medical AG, Zug (CH)

( * ) Notice: Subject to any disclaimer, the term of this patent is extended or adjusted under 35 U.S.C. 154(b) by 1030 days.

(21) Appl. No.: 16/981,994

(22) PCT Filed: Mar. 11, 2019

(86) PCT No.: PCT/EP2019/055967
§ 371 (c)(1),
(2) Date: Sep. 17, 2020

(87) PCT Pub. No.: WO2019/185335
PCT Pub. Date: Oct. 3, 2019

(65) Prior Publication Data
US 2021/0106758 A1    Apr. 15, 2021

(30) Foreign Application Priority Data

Mar. 26, 2018    (EP) .................................. 18164056

(51) Int. Cl.
*A61M 5/24*  (2006.01)
*A61M 5/315*  (2006.01)
(Continued)

(52) U.S. Cl.
CPC .......... *A61M 5/24* (2013.01); *A61M 5/31525* (2013.01); *A61M 5/3204* (2013.01);
(Continued)

(58) Field of Classification Search
CPC ........ A61M 5/24; A61M 5/3204; A61M 5/20; A61M 5/32; A61M 5/3202;
(Continued)

(56) References Cited

U.S. PATENT DOCUMENTS

| 11,857,767 | B2 * | 1/2024 | Bar-El .................... A61M 5/24 |
| 2009/0012471 | A1 | 1/2009 | Harrison |
| 2017/0173264 | A1 * | 6/2017 | Bendek ............... A61M 5/2033 |
| 2017/0259002 | A1 * | 9/2017 | Laiosa ................ A61M 5/2033 |

(Continued)

FOREIGN PATENT DOCUMENTS

| CN | 103167888 A | 6/2013 |
| CN | 104136059 A | 11/2014 |

(Continued)

OTHER PUBLICATIONS

International Search Report and Written Opinion for Int. App. No. PCT/EP2019/055967, completed May 14, 2019.

*Primary Examiner* — Joel M Attey
*Assistant Examiner* — Antarius S Daniel
(74) *Attorney, Agent, or Firm* — McDonnell Boehnen Hulbert & Berghoff LLP (57) ABSTRACT

A medicament container holder is presented having a body designed to accommodate at least a part of a medicament container and is arranged with a medicament delivery member surrounded by a needle shield; a holding element arranged at a proximal end of the body for holding a neck portion of the medicament container. The holding element being flexible in generally radial directions and support elements provided between the holding element and the body, where the support elements allow generally outwardly movement of the holding element from a first initial position during passing of the needle shield when the medicament container is placed in the medicament container holder, ensuring inwardly movement of the holding element after passing of the needle shield, returning the holding element towards the first initial position to a second position, and promoting generally inwardly action of the holding element to a third position during attachment of a needle shield remover to the needle shield.

16 Claims, 9 Drawing Sheets

(51) Int. Cl.
    *A61M 5/32*       (2006.01)
    *A61M 5/31*       (2006.01)

(52) U.S. Cl.
    CPC ............... *A61M 2005/2403* (2013.01); *A61M 2005/3115* (2013.01)

(58) Field of Classification Search
    CPC .... A61M 2005/206; A61M 2005/2403; A61M 2005/2407; A61M 2005/2411; A61M 2005/2418; A61M 2005/2477; A61M 2005/2437; A61M 2005/2433
    See application file for complete search history.

(56) References Cited

U.S. PATENT DOCUMENTS

2019/0060579 A1*   2/2019   Daniel ................... A61M 5/24
2019/0201634 A1*   7/2019   Newton .............. A61M 5/3213

FOREIGN PATENT DOCUMENTS

| | | |
|---|---|---|
| JP | 2014-530083 A | 11/2014 |
| JP | 2015-500125 A | 1/2015 |
| WO | 2007/083115 A1 | 7/2007 |
| WO | 2013/058697 A1 | 4/2013 |
| WO | 2013/089620 A1 | 6/2013 |
| WO | 2016/193356 A1 | 12/2016 |
| WO | 2016/193374 A1 | 12/2016 |
| WO | 2017/071909 A1 | 5/2017 |
| WO | 2017102175 A1 | 6/2017 |
| WO | 2018/015119 A1 | 1/2018 |
| WO | 2019/063267 A1 | 4/2019 |

* cited by examiner

MEDICAMENT CONTAINER HOLDER

CROSS REFERENCE TO RELATED APPLICATIONS

The present application is a U.S. National Phase Application pursuant to 35 U.S.C. § 371 of International Application No. PCT/EP2019/055967 filed Mar. 11, 2019, which claims priority to European Patent Application No. 18164056.6 filed Mar. 26, 2018. The entire disclosure contents of these applications are herewith incorporated by reference into the present application.

TECHNICAL AREA

The present application relates to a medicament container holder and in particular a medicament container holder with enhanced support capabilities.

BACKGROUND

A number of medicament delivery devices have been developed having different degrees of automatic features and functions such as auto-penetration, auto-injection, auto-retraction etc. Many of these medicament delivery devices are provided with a medicament container holder arranged to accommodate and securely hold a medicament container. For many designs of the medicament container holders, they gripping feature that supports a neck portion of the medicament container, which acts as a support surface in the proximal direction. However, with the introduction of so called rigid needle shields or RNS's, additional demands are put on the design of the medicament container holders. This is because the diameter of the RNS's often are the same or larger than the diameter of the barrel of the medicament container. Due to this, some different designs have been devised.

Document US 2009/012471 discloses a medicament container holder having a longitudinally extending opening giving the medicament container holder a C-shape as seen in a cross-section. The longitudinally extending opening allows a medicament container with an RNS to be mounted from the side, i.e. clipped into the medicament container holder. The proximal end of the medicament container holder is arranged with a reduced diameter that will cooperate with a neck portion of the medicament container for supporting the medicament container in the proximal direction, wherein the RNS is positioned proximally of the end of the medicament container holder. However, if the RNS is exposed to a force in the distal direction, for instance by attaching a needle shield remover to the RNS, the RNS might be pushed in the distal direction past the proximal end with the reduced diameter, wherein also the medicament container is pushed distally. This in turn may result in that the needle shield remover does not grip the RNS properly, whereby the RNS might not be removed when the needle shield remover is pulled in the proximal direction when the medicament delivery device is to be used. Also, a wrong position of the medicament container may cause a malfunction of the entire device because of drive mechanisms, comprising energized plunger rods, acting on the medicament container at wrong positions.

Another design of a medicament container holder is arranged with a proximal support member that can flex generally radially when a needle shield of a medicament container is pushed longitudinally trough the medicament container holder. Thus the support member is flexing out when the needle shield is passing and flexes back to its initial position after the needle shield has passed. Typically these support members have a tubular body with a slit giving them a generally C-shape as viewed from the front. However, these designs suffer from the same type of problems as the above described designs, wherein the support members might flex out in the radial direction when exposed to distally directed forces by an RNS, which in turn might cause the RNS to pass the support member.

There is thus a demand for improvements regarding medicament container holders that can handle medicament containers provided with needle shields of quite large diameters.

SUMMARY

The aim of the present disclosure is to remedy the drawbacks of the state of the art medicament container holders. This aim is obtained by a medicament container holder provided with the features according to the independent patent claim. The dependent patent claims form preferable embodiments of the disclosure.

According to a main aspect of the present medicament container holder, it comprises a medicament container holder comprising a body designed to accommodate at least a part of a medicament container. The medicament container may be arranged with a medicament delivery member surrounded by a needle shield.

Further a holding element may be arranged at a proximal end of the body for holding a neck portion of the medicament container, where the holding element may be flexible in generally radial directions. The medicament container holder may further comprise support elements provided between the holding element and the body, wherein the support elements may allow generally outwardly movement of the holding element from a first initial position during passing of the needle shield when the medicament container is placed in the medicament container holder. The support elements may further ensure inwardly movement of the holding element after passing of the needle shield, providing a return of the holding element towards the first initial position to a second position. In addition the support elements may promote generally inwardly action of the holding element to a third position during attachment of a needle shield remover to the needle shield.

Thus, the support elements of the medicament container holder are able to allow a needle shield to pass a holding element when a medicament container is placed in the medicament container holder. Once the needle shield has passed the holding element, the support elements are arranged to move the holding elements towards the initial position towards a second position behind the needle shield as seen in a proximal direction. Depending on tolerances of the medicament container and the medicament container holder the second position may be the same as the initial position. On the other hand, the support elements may contact the medicament container at the second position before they have reached the initial position. In any event, the support elements will ensure inwardly movement of the holding elements after passing of the needle shield.

Further, if a needle shield remover is attached to the needle shield, this will most likely exert a force in the distal direction of the needle shield such that the needle shield is moved in the distal direction and contacts a proximal surface of the holding elements. In order that the force on the holding elements will not cause them to move outwards and possibly allow the needle shield to pass the holding elements, the support elements promote generally inwardly action of the holding elements. The inwardly action may, depending on tolerances, entail that the holding elements are pressed with an increased force against the medicament container. On the other hand, if there is an initial gap between the holding elements and the medicament container, the inwardly action will entail moving the holding elements inwards until they contact the medicament container. In any event, the design of the support elements will effectively prevent any outward movement of the holding elements if they are exposed to forces from the needle shield during attachment of a needle shield remover.

Typically the holding element is arranged with a central passage having a diameter smaller than the outer diameter of the needle shield. Thus, the proximal end of the needle shield will enter the passage and force the holding element outwardly in order to pass.

Further, the holding element may be provided with a generally tubular section, and wherein a proximal end of the section may be arranged with an inwardly directed ledge designed to engage the neck portion of the medicament container, and where the tubular section may be arranged with a slit for providing the movement action of the holding element. Depending on the design and choice of material the holding element may either be bent or pivoted along a certain point or be provided with flexible elastic properties that gives a flexing bending action of the holding element.

As an alternative to a continuous ledge, the inwardly directed ledge may comprise a number of ledge sections. This design may also affect the movement action and in particular any flexing action of the holding element.

Further, there is a risk that a flange of the medicament container might be damaged during a dose of the medicament being delivered, once it hits on the medicament container holder under a strong force of the drive spring. This risk is caused by the tolerance of the length on the medicament container. The support elements with their inclination also can perform a function of length compensation for the tolerance of the length of the medicament container by enable the movement of the holding element along the longitudinal axis (L), therefore, reduces the risk of the damage on the flange during the dose of the medicament being delivered.

In addition, the support elements can also act as a damper for the medicament container under the force of drive spring while the dose of the medicament being delivered, and dissipate the spring force and prevent the damage of the medicament container.

According to a further aspect of the application, the support elements may comprise beams extending from the tubular body section to the body on each side of the slit; or comprises outwardly deformable beams extending from the tubular body section to the body. Preferably the beams may be inclined in relation to a longitudinal axis of the medicament container holder. This inclination promotes the inwardly action of the holding element when a force is applied by a needle shield remover that is pressed onto the needle shield. Especially the design where the beams have a narrower distance between them as seen in a circumferential direction at the attachment points of the tubular section than at the attachment points at the body.

The medicament container holder may further comprise an attachment element extending between the tubular section and the body and positioned generally opposite the slit as seen in a circumferential direction. With this solution, only one slit may be provided and with the attachment on the opposite side, providing two free and movable parts of the holding element. As an alternative the attachment element and an adjacent part of the inwardly directed ledge may be provided with a cut-out. This solution provides a flexing or moving action of the holding element with reduced force requirements.

These and other aspects of, and advantages with, the present disclosure will become apparent from the following detailed description of the disclosure and from the accompanying drawings.

BRIEF DESCRIPTION OF DRAWINGS

In the following detailed description of the disclosure, reference will be made to the accompanying drawings, of which FIG. 1 schematically shows a perspective view of elements from an example medicament delivery with a medicament container holder of the invention.

DETAILED DESCRIPTION

Figure 1:
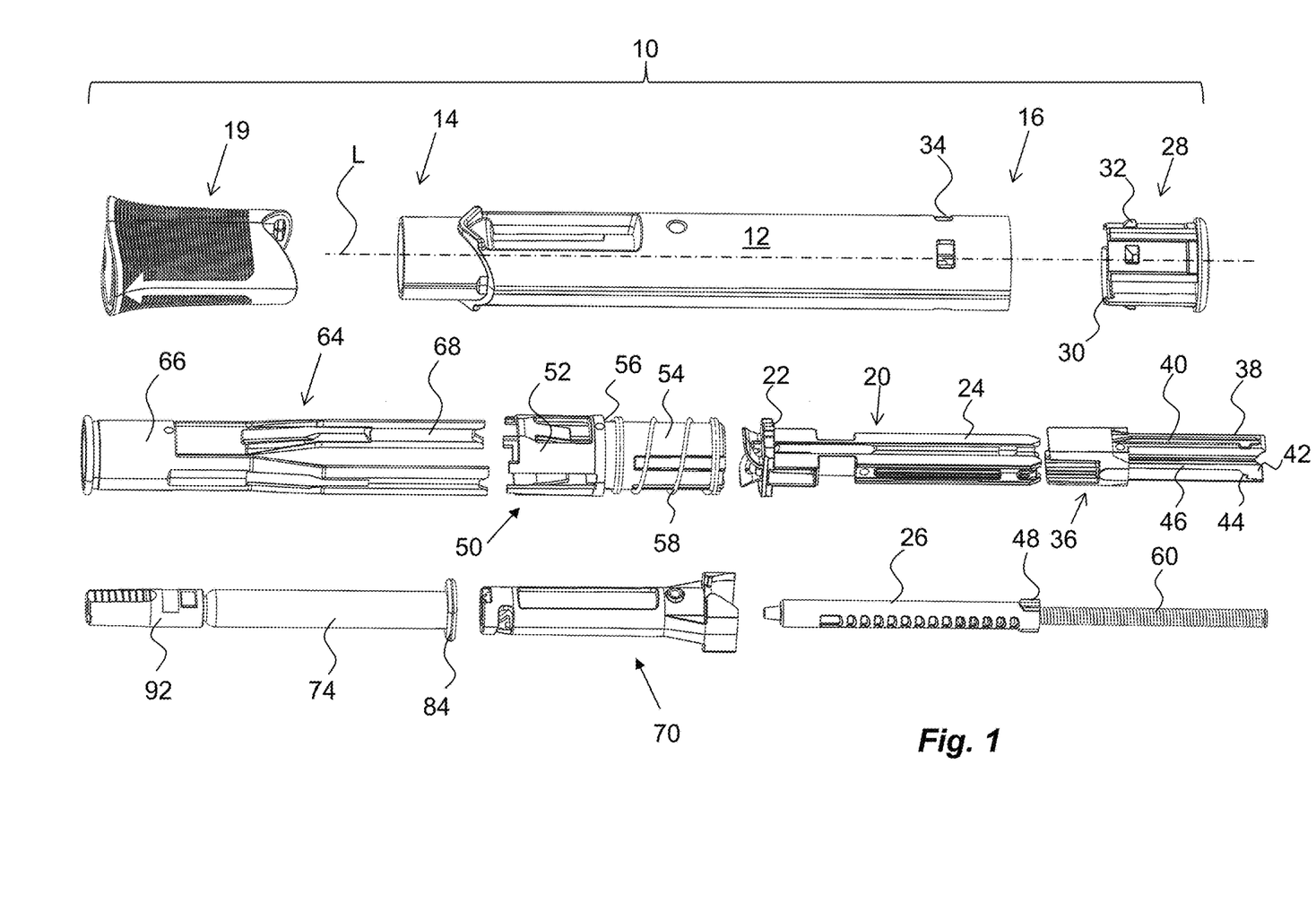

FIG. 1 shows an example of a medicament delivery device in which the intermediate structure according the present application may be utilized. The medicament delivery device 10 comprises an elongated housing 12 having a proximal end 14 and a distal end 16 and extending along a longitudinal axis L. The housing 12 has a transversal wall 18 having a central passage. A protective cap 19 is releasibly provided to the proximal end of the housing. Further, a power pack is provided comprising a plunger rod holder 20 with a proximal end plate 22. A central, circular, passage is arranged in the end plate 22. The end plate 22 is further arranged with distally directed arms 24 with curved inner surfaces that will enclose a plunger rod 26.

The distal ends of the arms 24 of the plunger rod holder are to cooperate with an end cap 28. The end cap 28 has a generally tubular body, which body has a proximal end surface forming a proximally directed ledge 30. Further the end cap 28 is arranged with outwardly directed protrusions 32 that are to interact with cut-outs 34 at a distal area of the housing 12, thereby locking the end cap 28 to the distal end of the housing 12.

Coaxial with and surrounding the plunger rod holder 20 is a slider 36. The proximal end surface of the slider 36 is designed to be in contact with a distal surface of the end plate 22 of the plunger rod holder 20. The slider 36 is arranged with two distally directed arms 38. The outer surfaces of the arms 38 are arranged with generally longitudinally extending ledges 40. The inner surfaces of the arms 38 are arranged with cut-outs 42 at their distal ends, wherein the cut-outs 42 are provided with inclined support surfaces 44. From the cut-outs, longitudinal grooves 46 are arranged, running all the way to the proximal end of the slider 36. The cut-outs 42 and the longitudinal grooves 46 are intended and designed to accommodate outwardly directed protrusions 48 on a distal end of the plunger rod 26.

Figure 2A:
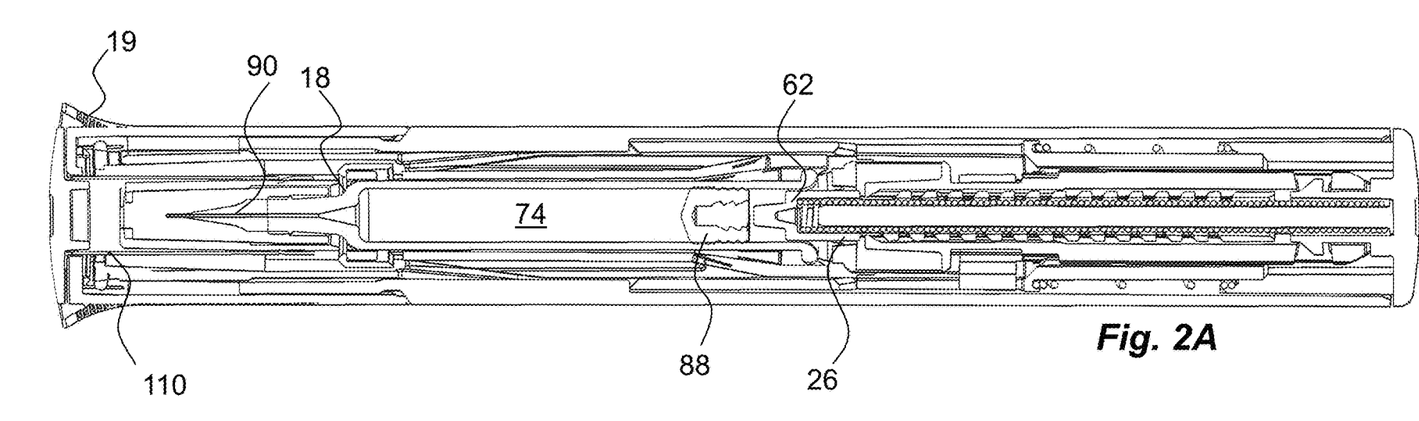
FIG. 2A schematically shows a side view of the medicament delivery device in an assembled configuration of FIG. 1.
Figure 2B:
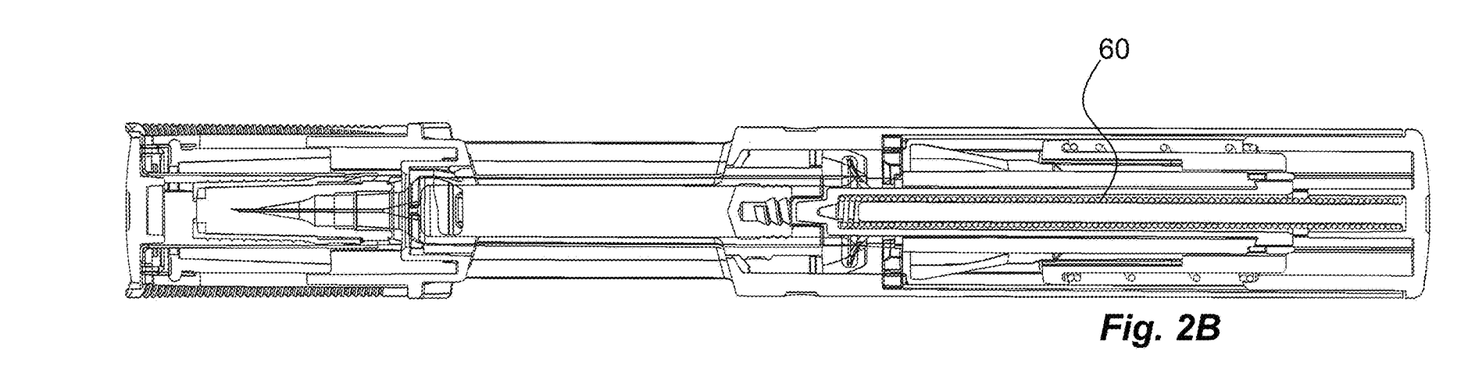
FIG. 2B schematically shows a side view of the medicament delivery device in an assembled configuration of FIG. 1.

Coaxial with and outside the slider 36 is an activator 50, hereafter named lock sleeve. The lock sleeve 50 has a generally tubular first proximal body part 52. The lock sleeve 50 is further arranged with a generally tubular second distal body part 54. The second body part 54 has a diameter smaller than the first part, creating a distally directed ledge 56. The inner surface of the second body part 54 is further arranged with longitudinally extending guide ledges, which guide ledges are to interact with the ledges 40 of the slider 36 as will be described. A lock sleeve spring 58 is arranged between the distally directed ledge 56 of the lock sleeve 50 and the proximally directed ledge 30 of the end cap 28, biasing the lock sleeve 50 in the proximal direction. Further a drive spring 60 is arranged inside the plunger rod 26 with a proximal end in contact with a transversal proximal end wall 62 of the plunger rod 50 and a distal end in contact with the end wall of the end cap 28, FIG. 2.

The medicament delivery device is further arranged with a needle shield 64, extending through a proximal passage of the housing 12. The needle shield 64 has a generally tubular body 66, which body 66 is arranged with a proximal circular passage. Further, two distally directed arms 68 are provided on a distal end of the body 66 of the needle shield 54, wherein the arms extend into the housing 12.

When the medicament delivery device is to be used, the user removes the protective cap 19. The next step is to place the proximal end of the needle shield 64 at a dose delivery site and press the medicament delivery device towards the site. The needle shield 64 will then move distally in relation to the rest of the medicament delivery device. Because the distal end surfaces of the needle shield 54 are in contact with the lock sleeve 50, the latter will also move distally, compressing the lock sleeve spring 58. Inner ledges of the lock sleeve 50 will slide along the outer ledges 40 of the slider 36 until the distal edge of a lock sleeve ledge is moved out of contact with outer ledge of the slider 36, thereby releasing the slider 36.

When now the slider 36 is released, its distal area is moved generally transversally by the force from the protrusions 48 of the tensioned plunger rod 26 on the inclined support surfaces 44 of the cut-outs 42 such that the protrusions 48 of the plunger rod 26 will move to the longitudinal grooves 46 on the inside of the slider 36. The plunger rod 26 is now free to move in the proximal direction by the drive spring 60. The movement of the plunger rod 26 will cause a dose of medicament to be delivered from a medicament container 74 provided with an injection needle 90, FIG. 2.

According to the present application, coaxial with and inside the needle shield 64 is a medicament container holder 70. The medicament container holder has a generally tubular body 72 in a first embodiment shown in FIGS. 3a-b, which body 72 is arranged with rectangular openings 73 on opposite sides. The medicament container holder 70 is further arranged with a distal section 76 having oppositely positioned surfaces 78 that are tapering outwards in the distal direction, where a distal area 80 of the tapering surfaces 78 is arranged as a support surface. The distal end of the medicament container holder 70 is arranged with a seat 82 for a flange 84, FIG. 1, of the medicament container 74. The medicament container 74 has an elongated tubular body, in which a stopper 88, FIG. 2, is arranged movable. The medicament delivery member 90, e.g. an injection needle, is in the embodiment attached to the proximal end of the medicament container. The medicament injection needle 90 is protected by a needle shield 92 that in the embodiment shown is a needle shield, and in particular a so called rigid needle shield or RNS.

Figure 3A:
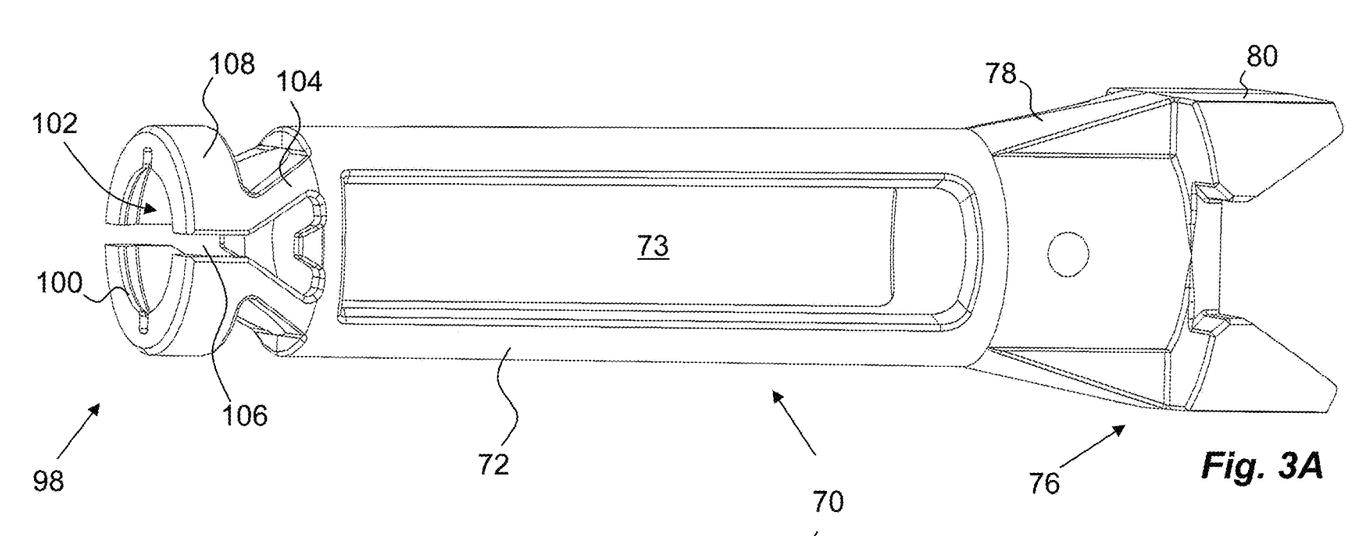
FIG. 3A schematically shows a perspective view of a first embodiment of the medicament container holder of the invention.
Figure 3B:
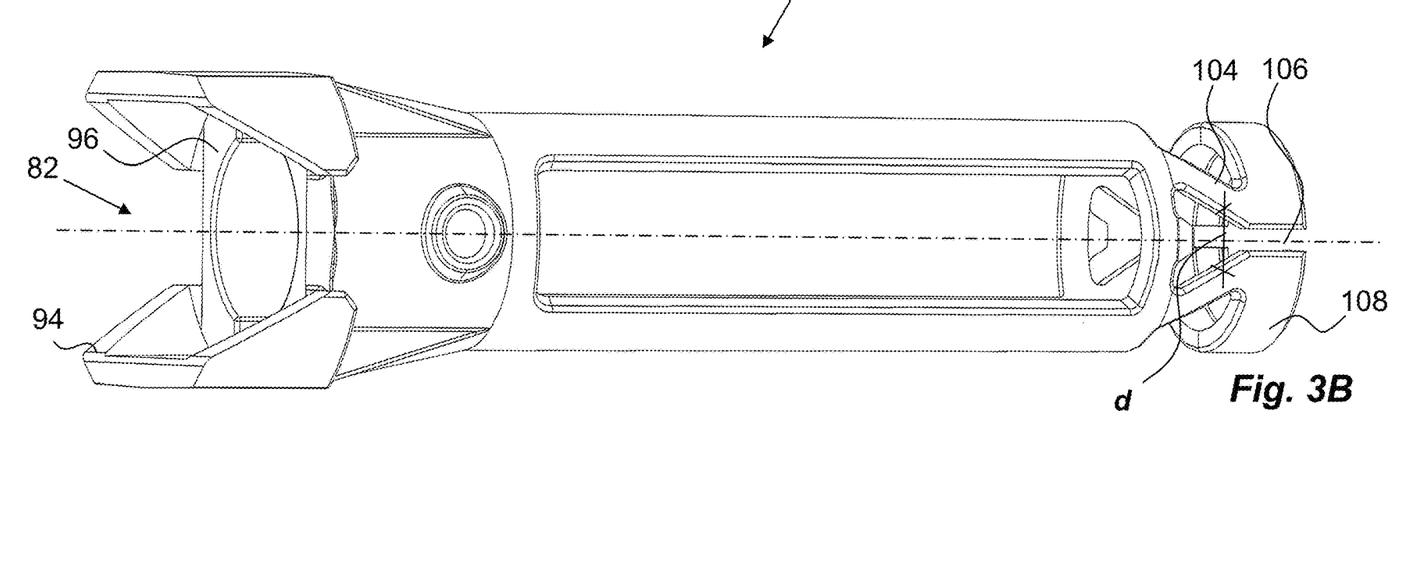
FIG. 3B schematically shows a perspective view of a first embodiment of the medicament container holder of the invention.

Moreover, either the side surfaces of the flange 84 of the medicament container 74 are surrounded by walls or wall sections 94, FIG. 3, of the seat 82 when assembled with the medicament container holder 70. The seat 82 is further arranged with a distally directed support surface 96 for contact with the proximal surface of the flange 84. At the proximal end of the medicament container holder 70 a generally tubular holding element 98 is arranged, FIG. 3, having a radially inwardly directed flange 100 at its proximal end, providing a circular passage 102 through which the needle shield 92 may pass. The holding element 98 is connected to the proximal end of the body 72 via support elements that in the embodiment shown are designed as beams or arms 104. As seen in the embodiment, the holding element 98 is provided with two slits 106 on opposite sides of the passage 102, such that the holding element 98 is split in two free parts in the form of arc-shaped elements 108. At the ends of the arc-shaped elements 108, the support elements 104 are attached, wherein the distal end of the support elements 104 are attached to the body 72. The support elements 104 are inclined in relation to a longitudinal axis L of the medicament container holder 70. The support elements 104 are inclined outwards in the sense that the distance d between two adjacent support elements increase in the distal direction that is seen for example in FIG. 3b with support elements 104I and 104II.

Figure 4A:
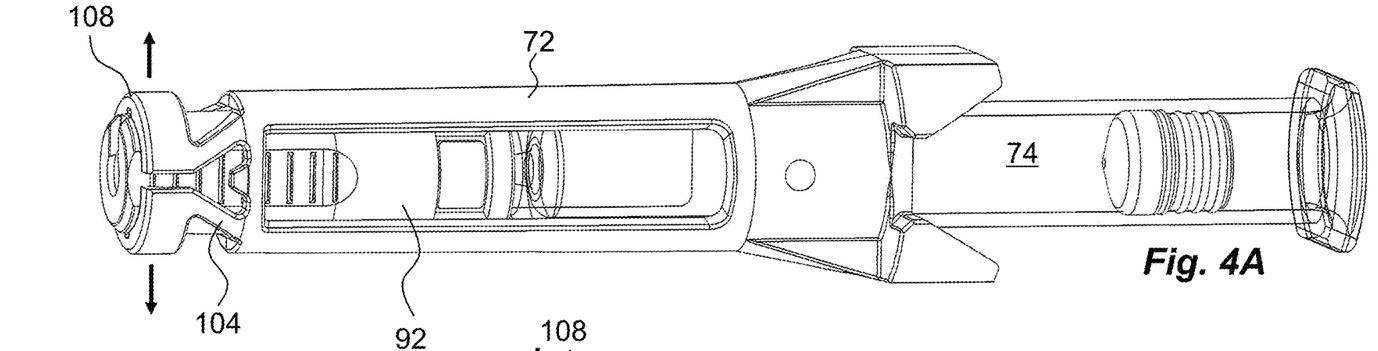
FIG. 4A schematically shows a perspective view of the medicament container holder of FIGS. 3A-3B while a medicament container is assembling into.

The function of the medicament container holder 70 will now be described. When a medicament container 74 with its needle shield 92 is to be assembled with the medicament container holder 70 it is inserted from the distal end. When the needle shield 92 comes in contact with the arc-shaped elements 108 of the holding element 98, the arc-shaped elements 108 will move in the generally radially opposite directions from the first initial position against the resilient force of the support elements 104, allowing passing of the needle shield 92, FIG. 4a. The thickness of the support elements 104 and the choice of material will determine the force needed to move the arc-shaped elements 108 so that the needle shield 92 is allowed to pass, and the design according to the present embodiment provide rather low force requirements for the needle shield 92 to pass.

Figure 4B:
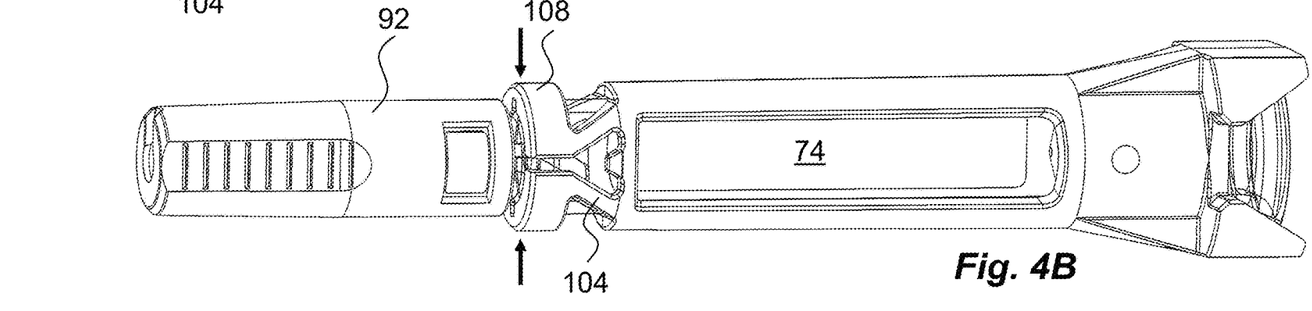
FIG. 4B schematically shows a perspective view of the medicament container holder of FIGS. 3A-3B while a medicament container is assembling into.

When the distal end of the needle shield 92 has passed the proximal surface of the support element, the arc-shaped elements 108 will flex radially inwards towards each other due to the resilient force of the support elements 104, FIG. 4b towards the initial position to a second position. Depending on the tolerances of the holding element 98 and in particular the medicament container 74 there are different scenarios as to the second position of the holding element 98 in relation to the neck portion of the medicament container 74. It could either be that the arc-shape elements 108 flex back to the initial unaffected first position, i.e. the second position is the first position, in which position the inner distal surfaces of the arc-shaped elements 108 are in contact with the outer surface of the neck portion of the medicament container 74. In this position, the flange 84 of the medicament container 74 may be in contact with the distal surface 96 of the seat 82 in the distal end of the medicament container holder 70 or there might be a gap between the flange 84 and the seat 82. On the other hand, there might be some gap between the arc-shaped elements 108 and the neck portion of the medicament container 74. In this position, the flange 84 is in contact with the seat 82 of the medicament container holder 74. A further scenario is where the inner distal surfaces of the arc-shaped elements 108 come in contact with the outer surface of the neck portion before they reach the initial position, whereby there will be some residual resilient force in the support elements 104 of the holding element 98. In this scenario the flange 84 is in contact with the seat 82 of the medicament container holder 70. In any event, the holding element 98 and/or the seat 82 prevent the medicament container 74 from moving in the proximal direction inside the medicament container holder 70.

When the medicament container holder 70 with the medicament container are placed in the medicament delivery device as seen in FIG. 4b, one assembly step is to attach a needle shield remover 110 at the proximal end of the housing of the medicament delivery device, which needle shield remover is attached to the protective cap 19. Thereby a tubular body of the needle shield remover 110 is pushed in the distal direction onto the needle shield, FIG. 4c. The diameter of the body of the needle shield remover 110 is slightly larger than the diameter of the needle shield 92, allowing the body to be pushed onto the needle shield 92. The needle shield remover 110 is further provided with grip elements 112 that in the embodiment shown are inwardly inclined and proximally directed grip elements, designed to come in contact with the outer surface of the needle shield 92 and to slide in relation to the needle shield 92 when the needle shield remover 110 is pushed onto the needle shield 92 but to grip into the material of the needle shield 92 when pulled in the proximal direction, locking the two to each other. However, the contact between the grip elements 112 and the needle shield 92 during assembly will create a force in the distal direction of the needle shield 92 whereby it will contact the proximal surface of the holding element 98, FIG. 4c, and exert a force in the distal direction on the arc-shaped elements 108.

Figure 4C:
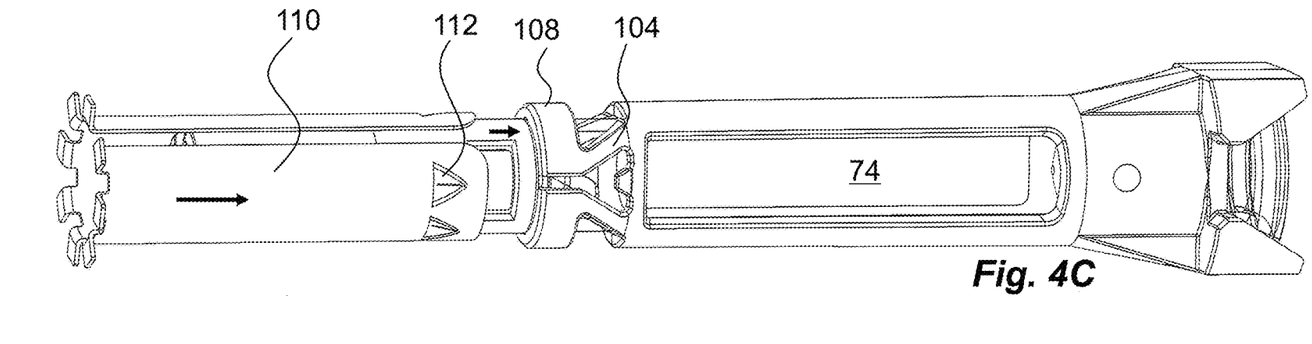
FIG. 4C schematically shows a perspective view of the medicament container holder of FIGS. 3A-3B while a medicament container is assembling into.

Now the design of the support elements 104 with their inclination as described will prevent the arc-shaped elements 108 from moving outwards, thereby preventing that the needle shield 92 passes through the passage 102 of the holding element 98. Instead, the inclination of the support elements 104 will urge the arc-shaped elements 108 inwards when such a force is applied in the distal direction. As mentioned above, if the arc-shaped elements 108 are in contact with the neck portion of the medicament container 74, they will be urged with more force against the neck portion. On the other hand, if there was a gap between the arc-shaped elements 108 and the neck portion as describe above, the force on the arc-shaped elements 108 will urge them inwards in the generally radial direction due to the support elements 104 until they come in contact with the neck portion of the medicament container 74. In any event, a force from the needle shield 92 in the distal direction will strengthen the contact between the arc-shaped elements 108 and the neck portion, effectively preventing any passing of the needle shield 92 through the passage of the holding element 98.

Depending on the type of material and its properties, the arc-shaped elements 108 may either be relatively rigid in the sense that they will retain more or less the same arc shape when the needle shield is passing. As an alternative, the material of the arc-shaped elements 108 may be such that they bend outwardly or straighten out somewhat when the needle shield 92 passes due to that the main contact points between the needle shield 92 and the arc-shaped elements 108 occur adjacent the slits 106 of the holding element 98.

In addition, the support elements 104 with their inclination also can perform a function of compensating the length tolerance of medicament container by enable the movement of the holding element 98 along the longitudinal axis (L). Especially applied in the design with the inner distal surfaces of the arc-shaped elements 108 are in contact with the outer surface of the neck portion of the medicament container 74 and the there is a gap between the flange 84 of the medicament container 74 and the seat 82 of the medicament container holder 70. In this embodiment, a shorter medicament container is received in the medicament container holder 70 may create a risk of damage on the flange 84 of the medicament container during the dose of the medicament being delivered since the flange 84 being too close to the medicament container holder 70. This risk can be reduce by remaining a proper gap between the flange 84 of the medicament container 74 and the medicament container holder 70; which can be achieved by pressing the holding element 98 toward the body 72 and sloping more the support elements 104. Therefore, while the dose of the medicament being delivered, since the flange 84 is remained a distance from the medicament container holder 70, even under the strong force of the drive spring 60, it will not contact the medicament container holder 70 and damage itself. Further, the resilience of the support elements 104 can also act as a damper for the medicament container 74 during the dose of the medicament being delivered. The deformation of the support elements 104 under the force of the drive spring 60 dissipates the spring force applied on the medicament container 74, therefore, reduces the risk of damaging the medicament container 74.

Figure 5A:
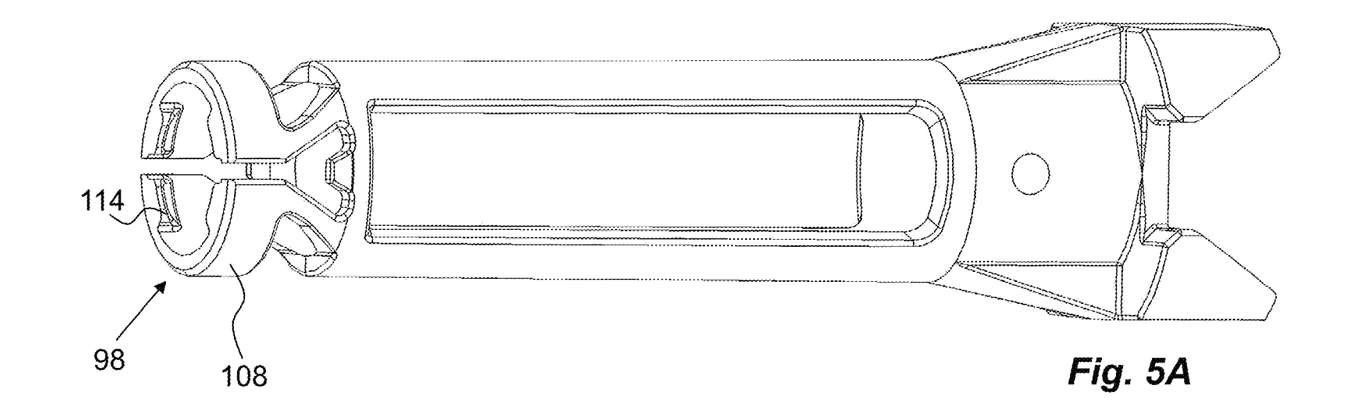
FIG. 5A schematically shows a perspective view of the medicament container holder of FIGS. 3A-3B with a reduced inwardly directed flanges to discreet elements or protrusions.
Figure 5B:
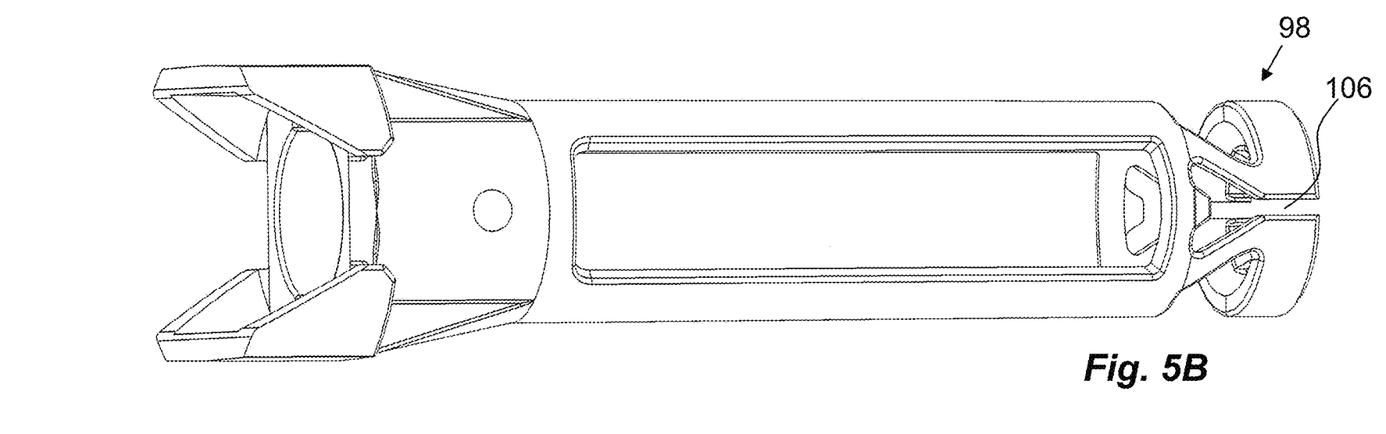
FIG. 5B schematically shows a perspective view of the medicament container holder of FIGS. 3A-3B with a reduced inwardly directed flanges to discreet elements or protrusions.

FIG. 5 shows a slight variant of the first embodiment. Here the inwardly directed flanges have been reduced to discrete elements or protrusions 114 adjacent the slits 106 of the holding element 98. This design even further facilitates the passing of the needle shield 92 through the support element, although still providing sufficient blocking support against the neck portion of the medicament container.

Figure 6A:
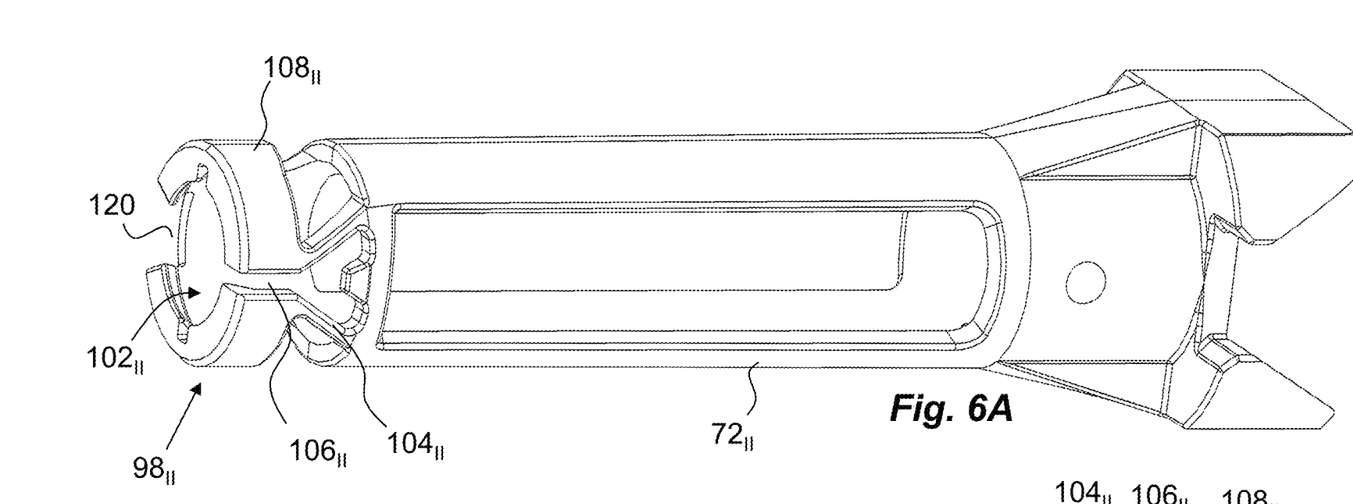
FIG. 6A schematically shows a perspective view of a second embodiment of the medicament container holder of the invention.
Figure 6B:
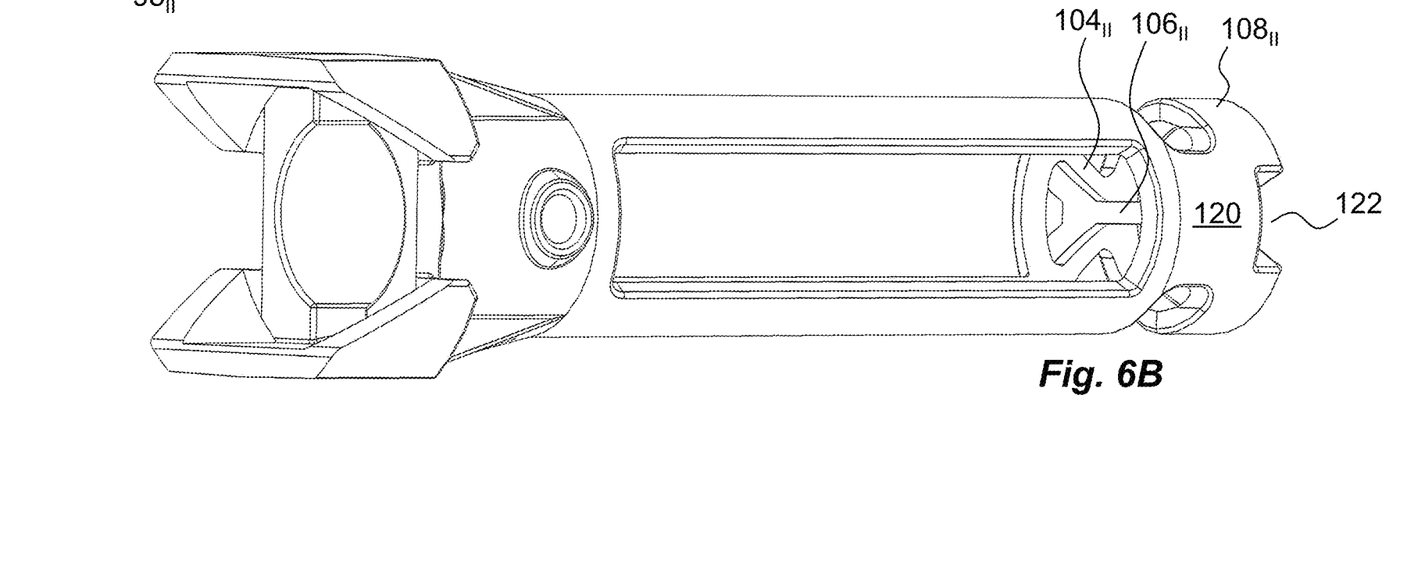
FIG. 6B schematically shows a perspective view of a second embodiment of the medicament container holder of the invention.

FIG. 6 show a further embodiment of the medicament container holder. In this embodiment the holding element $98_{II}$ is provided with only one slit $106_{II}$, wherein the holding element $98_{II}$ is in the form of a C-shape with its central passage $102_{II}$. Each end of the C is provided with an inclined support element $104_{II}$ as described above. At the opposite side of the slit $106_{II}$ as seen along the circumference, a rigid base or attachment element 120 connects the holding element $98_{II}$ to the proximal end of the body $72_{II}$. Further the base element 120 is provided with a cut-out 122 at its proximal area. The second embodiment functions much in the same way as the previous embodiment wherein the free parts $108_{II}$ of the holding element $98_{II}$ between the base element 120 and the slit $106_{II}$ move generally radially outwards. In this regard there are two scenarios regarding material and design. One solution is that the free parts $108_{II}$ of the holding element $98_{II}$ are made of a rather rigid material and the outward movement occurs through a bending action at the attachment point with the base element 120. In connection to this, the free parts $108_{II}$ of the holding element $98_{II}$ at the connection point with the base element 120 may be weakened by reducing material so as to facilitate the bending action, wherein the reducing of material may be the cut-out 122 as described above. As an alternative, the free parts $108_{II}$ of the holding element $98_{II}$ are made of a rather resilient material wherein the free parts $108_{II}$ bend outwardly or straighten out somewhat when the needle shield $92_{II}$ passes.

Figure 7A:
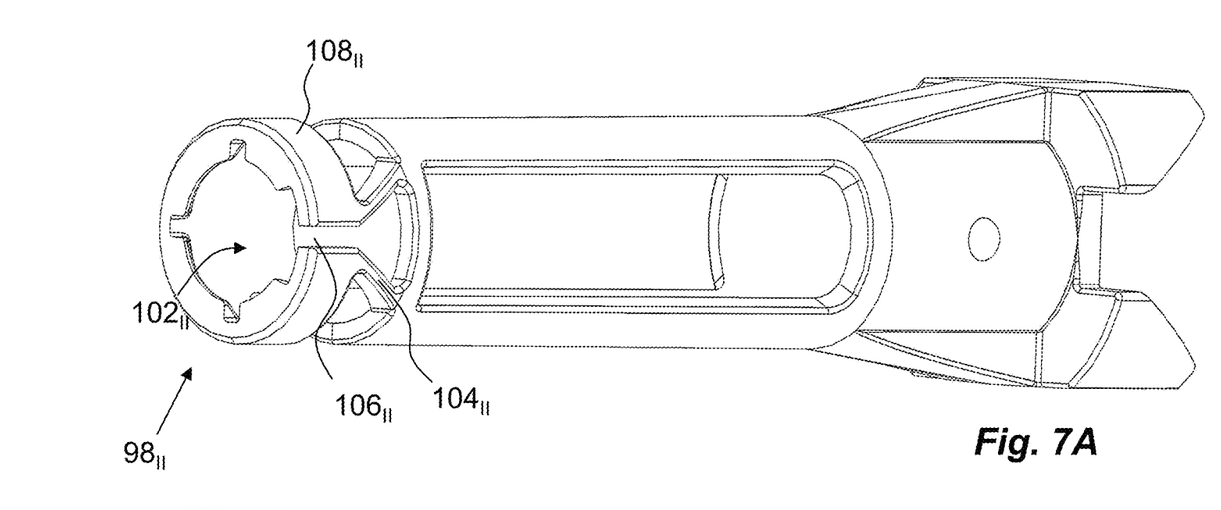
FIG. 7A schematically shows a perspective view of the medicament container holder of FIGS. 6A-6B with a wider extension around a circumference of a holding element.
Figure 7B:
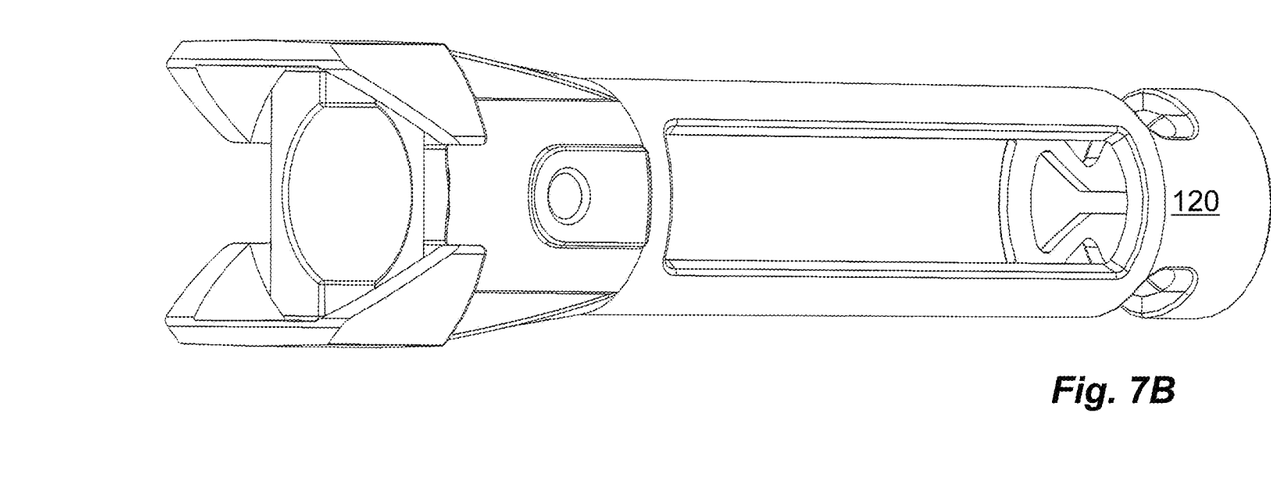
FIG. 7B schematically shows a perspective view of the medicament container holder of FIGS. 6A-6B with a wider extension around a circumference of a holding element.

FIG. 7 shows a variant of the second embodiment wherein the base element 120 has a wider extension around the circumference of the holding element 98, giving shorter free parts 108 of the holding element 98 and/or that the cut-out 122 as described earlier has been omitted. This may be to increase the resistance against radial movement of the free parts 108. This may be particularly important to ensure that the free parts 108 will not easily flex outwards when a force is exerted on the proximal surface of the support element by the distal end of the needle shield 92 when a needle shield remover 110 is attached as described above.

Figures 8A, 8B:
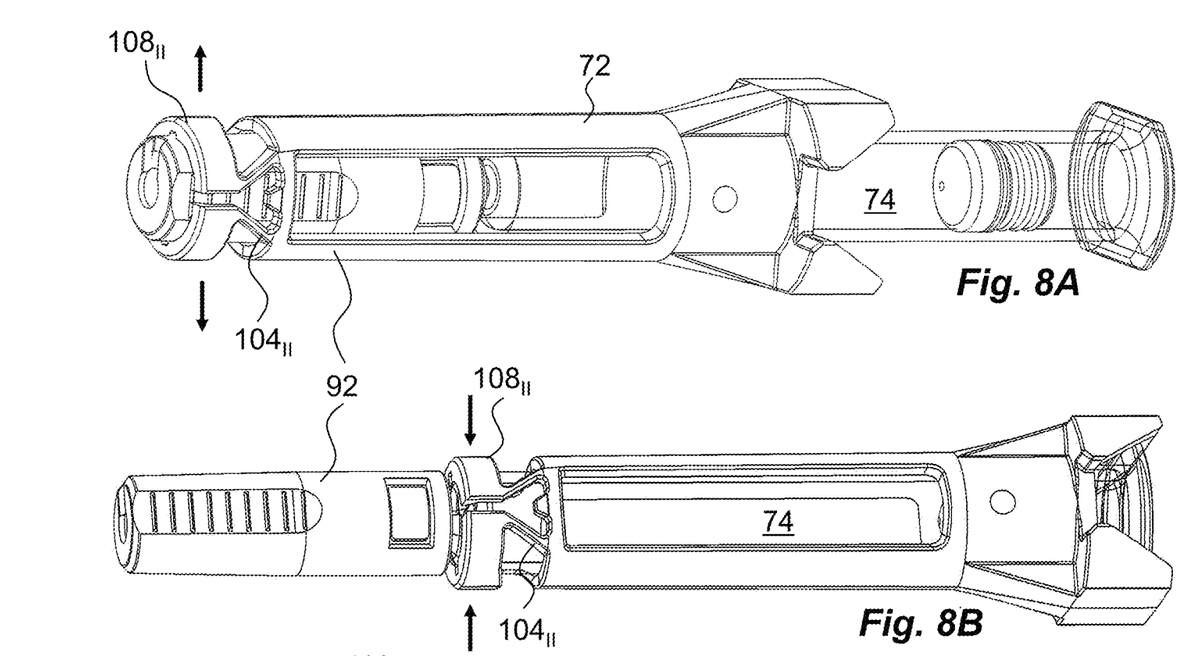
FIG. 8A schematically shows a perspective view of the medicament container holder of FIGS. 6A-6B while a medicament container is assembling into.
FIG. 8B schematically shows a perspective view of the medicament container holder of FIGS. 6A-6B while a medicament container is assembling into.
Figure 8C:
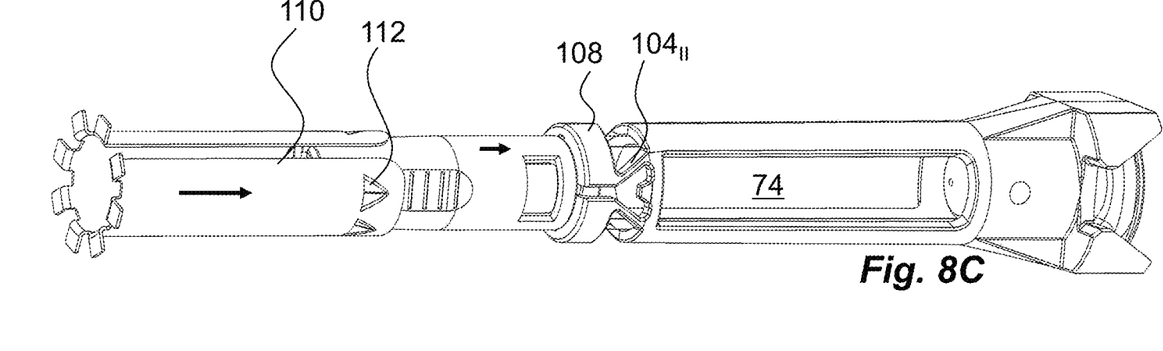
FIG. 8C schematically shows a perspective view of the medicament container holder of FIGS. 6A-6B while a medicament container is assembling into.

The second embodiment functions in generally the same way as the first embodiment, as seen in FIGS. 8a-c.

Figure 9A:
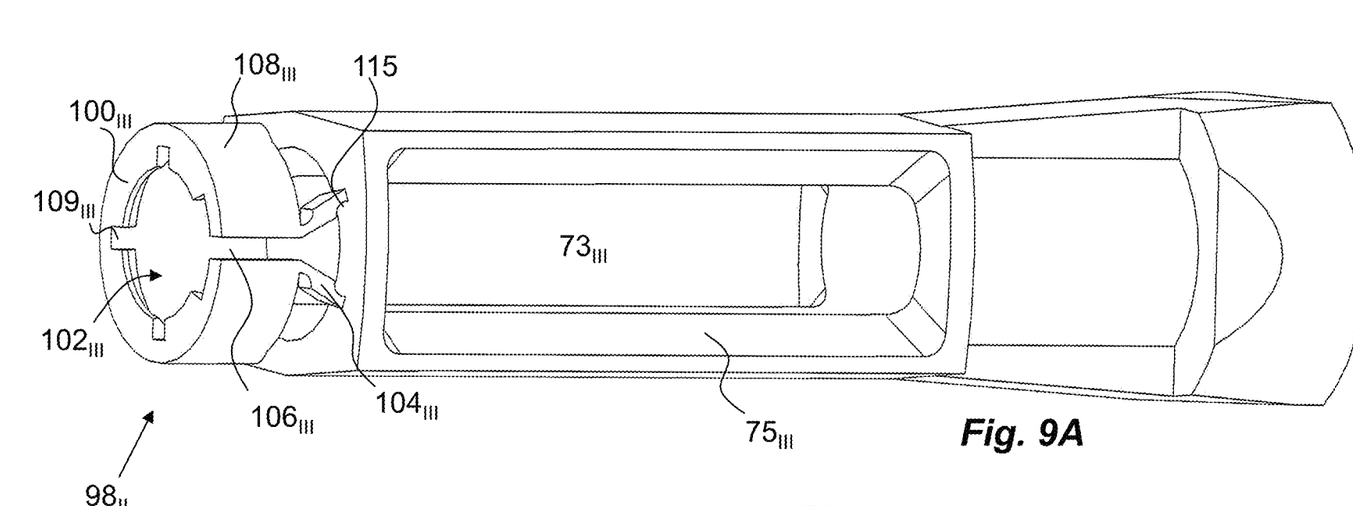
FIG. 9A schematically shows a perspective view of third embodiment of the medicament container holder of the invention.
Figure 9B:
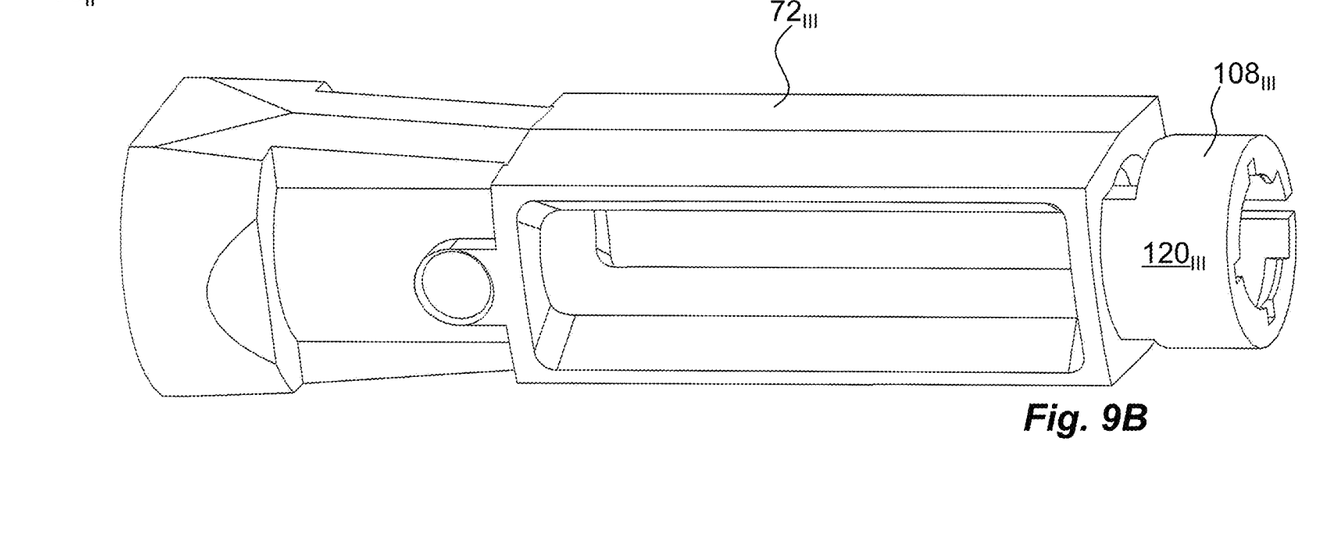
FIG. 9B schematically shows a perspective view of third embodiment of the medicament container holder of the invention.

A third embodiment is shown in FIGS. 9a-b. Here the medicament container holder $70_{III}$ may have a generally rectangular body $72_{III}$, which body $72_{III}$ is arranged with rectangular openings $73_{III}$ on opposite sides. The openings $73_{III}$ are arranged with inwardly directed wall sections $75_{III}$ ending in a semi-circular section of the body $72_{III}$ for supporting a medicament container. At the proximal end of the medicament container holder $70_{III}$ a generally tubular holding element $98_{III}$ is arranged, having a radially inwardly directed flange $100_{III}$ at its proximal end, providing a circular passage $102_{III}$ through which the medicament delivery member 92 may pass. The holding element $98_{III}$ is connected to the proximal end of the body $72_{III}$ via an arc-shaped base element $120_{III}$. At the opposite side of the base element $120_{III}$, a slit $106_{III}$ is provided through the holding element $98_{III}$ with its flange $100_{III}$ giving the holding element $98_{III}$ a C-shape with free parts $108_{III}$ when viewed from the proximal end. Three more slits $109_{III}$ are arranged equidistantly around the flange $100_{III}$. At the ends of the "C" adjacent the slit $106_{III}$, two distally directed support elements $104_{III}$ are arranged, FIG. 8, which support elements $104_{III}$ are connected to the proximal end of the body $72_{III}$. The support elements $104_{III}$ are somewhat inclined outwards in the distal direction and have thinned out portions 115 adjacent the connection points.

Also this embodiment functions generally as the previous embodiments. However, the holding element $98_{III}$ is in this embodiment somewhat more rigid as the free parts $108_{III}$ of the holding element $98_{III}$ is somewhat wider than for the previous embodiments as seen in the figures. On the other hand, the thinned-out portions 115 of the support elements $104_{III}$ will provide a somewhat lesser resistance when the support element flexes outwards in the generally radial direction.

It is to be understood that the present application described above and shown in the drawings is to be regarded as can be modified in many ways within the scope of the patent claims.

The invention claimed is:

1. A medicament container holder comprising:
    a body designed to accommodate at least a part of a medicament container, which medicament container has a longitudinal axis and is arranged with a medicament delivery member surrounded by a needle shield;
    at least two support elements extending from a proximal end of the body, where the support elements are flexible and inclined inwardly relative to a plane incorporating the longitudinal axis and that bisects the body longitudinally; and
    a holding element arranged at a proximal end of the support elements and spaced a distance proximally from the proximal end of the body, where the holding element has a through hole with a diameter that is configured for holding a neck portion of the medicament container, the holding element being flexible in generally radial directions; and
    wherein the support elements,
    allow outwardly movement of the holding element from a first initial position during passing of the needle shield when the medicament container is placed in the medicament container holder;
    ensure inwardly movement of the holding element after passing of the needle shield, such that the holding element can move towards the first initial position to a second position; and
    promote inwardly action of the holding element to a third position during attachment of a needle shield remover to the needle shield, where the diameter of the through hole is less when the holding element is in the third position as compared to the second position; and
    are configured to flex inwardly relative to the plane to cause the holding element to move axially in a distal direction relative to the proximal end of the body such that the distance between the holding element and the proximal end of the body is decreased.

2. The medicament container holder according to claim 1, wherein the holding element is arranged with the through hole having a diameter smaller than the outer diameter of the needle shield.

3. The medicament container holder according to claim 1, wherein the holding element is provided with a generally tubular section, and wherein a proximal end of the section is arranged with an inwardly directed ledge designed to engage the neck portion of the medicament container, and where the tubular section is arranged with a slit for providing movement action of the holding element.

4. The medicament container holder according to claim 3, wherein the inwardly directed ledge comprises a number of ledge sections.

5. The medicament container holder according to claim 3, wherein the support elements comprise beams extending from the tubular section of the holding element to the body on each side of the slit.

6. The medicament container holder according to claim 5, wherein the beams are inclined in relation to the longitudinal axis of the medicament container holder.

7. The medicament container holder according to claim 6, where the beams have a narrower distance between them as seen in a circumferential direction at the attachment points of the tubular section of the holding element than at the attachment points at the body.

8. The medicament container holder according to claim 3, further comprising an attachment element extending between the tubular section and the body and positioned generally opposite the slit as seen in a circumferential direction.

9. The medicament container holder according to claim 8, wherein the attachment element and an adjacent part of the inwardly directed ledge is provided with a cut-out.

10. The medicament container holder according to claim 1, wherein the support elements are further configured to dissipate the force of a drive spring while a dose of the medicament being delivered.

11. A medicament delivery device comprising a medicament container holder according to claim 1.

12. A medicament container holder comprising:
a body designed to accommodate a medicament container comprising a medicament delivery member surrounded by a removable needle shield;
a holding element positioned at a proximal end of the support element and spaced a distance proximally from a proximal end of the body, where the holding element has a through hole with a diameter that is configured for engaging a neck portion of the medicament container, where the holding element comprise at least two flexible proximally projecting arc-shaped holders that are configured to flex radially; and
support elements provided between the arc-shaped holders and the body, where the support elements:
allow outwardly radial movement of the arc-shaped holders to a first position when the needle shield is pushed axially in the proximal direction during placement of the medicament container in the medicament container holder, and
allow an axial distal movement of the arc-shaped holders along a longitudinal axis relative to the proximal end of the body such that the distance between the holding element and the proximal end of the body is decreased.

13. The medicament container of claim 12, wherein the support elements further ensure radial inward movement of the arc-shaped holders towards the neck portion and to a second position and promote radial inwardly movement of the arc-shaped holders to a third position during attachment of a needle shield remover to the needle shield.

14. The medicament container holder of claim 12, wherein the support elements are further configured to dissipate a biasing force of a drive spring during delivery of a dose of medicament.

15. The medicament container holder of claim 12, wherein the holding element further comprises a central passage having a diameter smaller than the outer diameter of the needle shield, and
wherein a proximal end of the arc-shaped holders comprises inwardly directed ledges designed to engage the neck portion of the medicament container.

16. The medicament container holder of claim 12, wherein the support elements comprise beams extending from a proximal end of the body and from the arc-shaped holders, and wherein the beams are inclined in relation to a longitudinal axis of the medicament container holder.

* * * * *